United States Patent [19]

Freeman

[11] Patent Number: 5,507,719
[45] Date of Patent: Apr. 16, 1996

[54] ORTHOTIC CALIPER

[75] Inventor: Mark J. Freeman, Camberley, England

[73] Assignee: Hugh Steeper Limited, London, United Kingdom

[21] Appl. No.: 213,052

[22] Filed: Mar. 15, 1994

[30] Foreign Application Priority Data

Mar. 19, 1993 [GB] United Kingdom ............... 9305748

[51] Int. Cl.$^6$ ................................................ A61F 5/00
[52] U.S. Cl. ..................... 602/26; 602/16; 602/20; 602/23; 16/292; 16/371; 16/374
[58] Field of Search .................. 602/16, 26, 20, 602/23; 16/292, 371, 374

[56] References Cited

U.S. PATENT DOCUMENTS

| 4,485,808 | 12/1984 | Hepburn . | |
|---|---|---|---|
| 4,881,299 | 11/1989 | Young et al. | 602/16 |
| 4,886,054 | 12/1989 | Castillo et al. . | |
| 5,038,763 | 8/1991 | Wiggins . | |
| 5,201,776 | 9/1993 | Freeman | 602/26 X |

FOREIGN PATENT DOCUMENTS 2260083   4/1993   United Kingdom .

*Primary Examiner*—Richard J. Apley
*Assistant Examiner*—Kim M. Lee
*Attorney, Agent, or Firm*—Dorn, McEachran, Jambor & Keating

[57] ABSTRACT

An orthotic caliper having at least two lockable steels for attachment to the respective limb members of the human body and having a locking pivotal connection between the steels, characterized by a releasable locking member which can be loaded in compression by the steels and which acts directly on at least one of the steels, and preferably on both of them, to lock them in a desired position when so loaded.

8 Claims, 3 Drawing Sheets

ORTHOTIC CALIPER

FIELD OF THE INVENTION

This invention relates to orthotic calipers comprising at least two pivotally-connected "steels" for attachment to the respective limb members of the human body. It is especially concerned with calipers provided with locking knee joints.

DESCRIPTION OF THE PRIOR ART

In GB-A-2,260,083 we have described an orthotic caliper of the construction outlined above having a pivotal connection between the two steels which is adapted to be held in a specific locked position by a releasable catch. In a particular construction illustrated in that Specification the pivotal connection takes the form of locking links which do not go overcentre, while the releasable catch takes the form of a hook having an angled engagement to take up play in the linkage formed by the locking links.

SUMMARY OF THE INVENTION

The present invention constitutes a development of that described and illustrated in GB-A-2,260,083. In essence, the new orthotic caliper which we have devised comprises a locking member which is loaded in compression by the steels and which acts directly on at least one steel, and preferably both steels, of the caliper. This locking member takes the place of the locking links provided in the earlier form of caliper mentioned above.

BRIEF DESCRIPTION OF THE DRAWINGS

In order that the invention might be thoroughly understood, a specific example of an orthotic caliper in accordance with it will now be described with reference to the accompanying drawings in which.

DESCRIPTION OF THE PREFERRED EMBODIMENT

Figure 1:
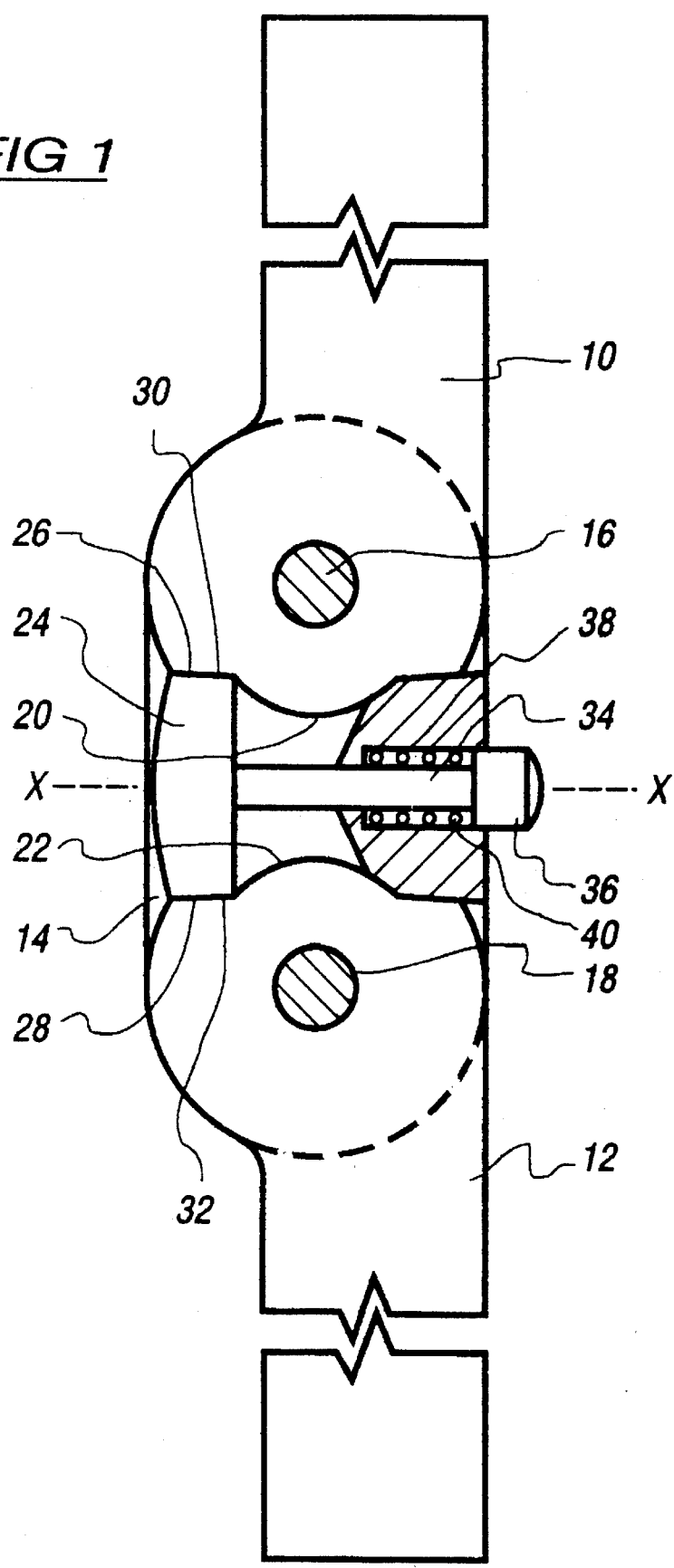
FIG. 1 is a part-sectional side view of the main portion of the caliper.

The orthotic caliper shown in the drawings comprises an upper steel 10 and a lower steel 12 which are provided with straps (not shown) or other fastening means whereby the steels can be attached to respective limb members of the human body. Normally the caliper would be used for attachment to the limb members of a leg, the upper steel 10 being attached to the thigh of the leg and the lower steel 12 being attached to the shin of the leg.

Figure 2:
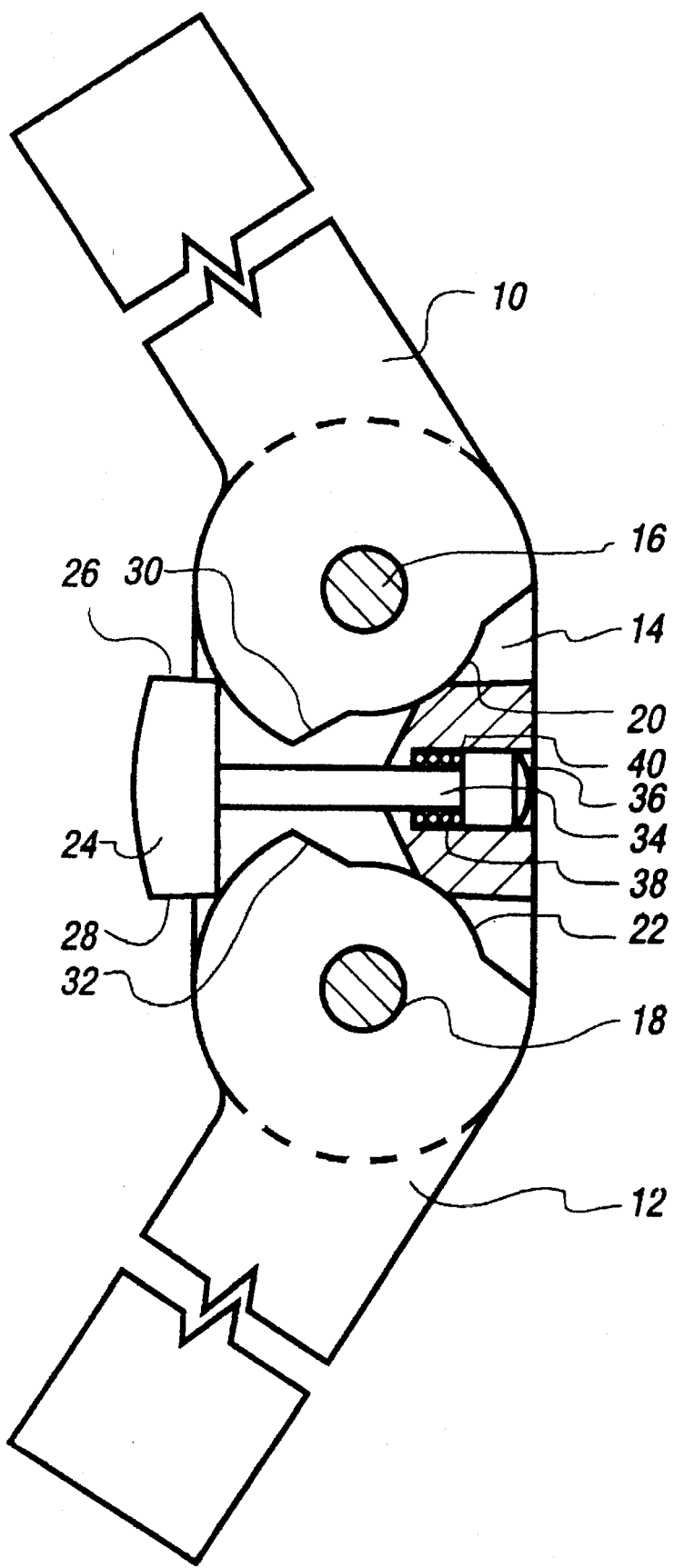
FIG. 2 is a view similar to FIG. 1 but with the two steels of the caliper at an obtuse angle with respect to each other.
Figure 3:
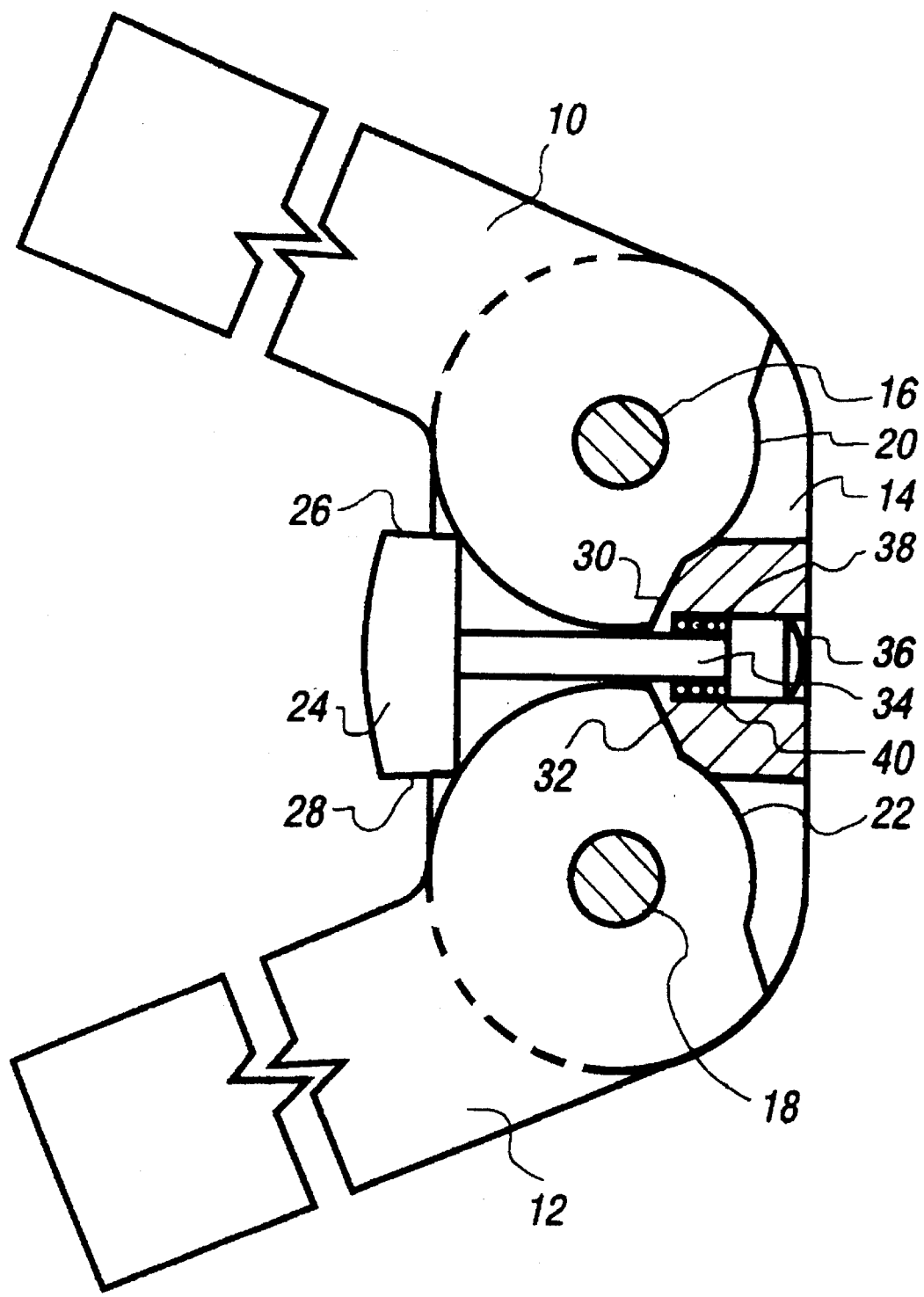
FIG. 3 is a view similar to FIGS. 1 and 2 but with the two steels at an acute angle with respect to each other.

The two steels 10 and 12 are pivotally connected together by a single link 14, the link 14 having a pivotal connection at 16 with the upper steel 10 and a pivotal connection 18 with the lower steel 12. This permits the two steels 10 and 12 to pivot about their respective pivotal axes 16 and 18 into a variety of angular positions two of which are shown by way of example only in FIGS. 2 and 3.

As will be seen, there is a gap between the lower end surface 20 of the upper steel 10 and the upper end surface 22 of the lower steel 12. Arranged for movement along a line X—X is a wedge 24 having flat surfaces 26 and 28 adapted to abut corresponding surfaces 30 and 32 on the end surfaces 20 and 22 of the steels 10 and 12. The wedge 24 has a rod 34 extending along the line X—X, the rod 34 being provided at the end remote from the wedge with a plunger or piston 36 which is movable within a cylindrical chamber 38. This cylindrical chamber is formed in a portion of the link 14.

The construction is such that, in operation of the caliper, the wedge 24 acts as a locking member which is loaded in compression by the steels. Further, this new design of caliper makes use of friction forces to pull the locking wedge 24 into engagement with the surfaces 30 and 32 on the steels 10 and 12 once a compression spring 40 within the cylindrical chamber 38 has brought the wedge into a position of initial engagement with those surfaces. In addition to this, the frictional forces hold the wedge in position whilst under load.

A novel feature of the caliper is that the flexion locking surfaces 30 and 32 are machined directly onto or into the upper and lower steels 10 and 12, so that these two surfaces form, in effect, a slot into which the locking wedge 24 fits tightly. As will be appreciated, the manner in which the locking wedge is mounted allows it to "float" to some extent so that it centralizes between the locking surfaces 30 and 32.

The locking surfaces 30 and 32 on the two steels are preferably flat, which means that they can be easily ground to high accuracy before final assembly of the caliper, thereby avoiding the need for final adjustment by filing the locking surfaces.

A further important feature of the caliper is that the pivotal connection between the two steels comprises two spaced-apart pivot points 16 and 18 which thus provide the joint with dual pivots. This allows it to follow the true centre of rotation of the patient's knee.

It is to be noted that, in the extended position of the steels shown in FIG. 1, the plunger or piston 36 projects outwardly from its cylindrical chamber 38 so as to serve as a push-button. This makes for easy operation of the caliper to release it from the locked position shown in FIG. 1. It is, however, to be understood that similar leavers or other additional means can be combined with the plunger or piston 36 to suit individual patients having special requirements.

The compressive loading of the wedge 24 between the two steels results in a very considerable increase in strength as compared to other calipers on the market. As far as we are aware existing calipers all suffer from some shear loading in their locking components, and this is often a source of failure. In addition to all this, the simplicity of the components used in the caliper described above makes the manufacture and assembly of the caliper less expensive that existing products.

Yet another advantage of the invention is that the caliper can be shaped to suit the patient's knee much more closely than with other calipers used hitherto.

Existing calipers sometimes use pivoting locking members provided with curved locking surfaces. This generally is the disadvantage that the number of associated components required—with their inter-dependent tolerance problems—frequently requires manual adjustment of the locking surfaces. In addition to this, the curved locking surfaces cannot essentially be formed "true".

I claim:

1. An orthotic caliper having at least two steels for attachment to two respective limb members of the human body, pivotal connection means connecting the two steels together so as to form a pivotal joint between the steels, the pivotal connection means thereby allowing the steels to rotate with respect to each other so as to permit the steels to take up a variety of angular positions with respect to each other, a releasable locking member arranged to abut and thereby act directly on at least one of the steels to lock the steels in a predetermined desired position against rotational movement in both directions relative to each other, said desired position being selected from the variety of relative positions which the steels are able to take up, and means on the steels which act on the locking member to apply compressive forces to said member when the steels are locked in said desired position, said compressive forces serving to hold the locking member in its locking position, and the releasable locking member being free to move, as the steels are brought into said desired position, in order to abut the said surface on said one steel.

2. An orthotic caliper according to claim 1, wherein a gap is provided between opposed end surfaces on the two steels, and wherein the locking member is a wedge provided with surfaces adapted to abut corresponding surfaces on the steels.

3. An orthotic caliper according to claim 2, wherein the wedge frictionally engages said corresponding surfaces on the steels to hold the wedge in position by friction while the wedge is under load.

4. An orthotic caliper according to claim 2 or claim 3, wherein the surfaces of the steels on which the wedge abuts are flat surfaces machined directly on to or into the steels so that a slot is formed into which the locking wedge fits tightly.

5. An orthotic caliper according to claim 1, wherein the pivotal connection means between the two steels comprises two spaced-apart pivot points so that the joint has dual pivots.

6. An orthotic caliper according to claim 2, wherein the wedge has a rod which is provided at the end remote from the wedge with a plunger or piston movable within a cylindrical chamber.

7. An orthotic caliper according to claim 6, wherein the plunger or piston projects outwardly from the cylindrical chamber so as to serve as a push-button in order to release the caliper from its locked position.

8. An orthotic caliper according to claim 1, wherein spring means are provided to urge the locking member into a locking position.

* * * * *